United States Patent
Mitchell

(10) Patent No.: US 8,690,933 B2
(45) Date of Patent: Apr. 8, 2014

(54) SYSTEM AND METHOD FOR TREATING SYMPTOMS OF RESTLESS LEGS SYNDROME

(75) Inventor: Ulrike Mitchell, Provo, UT (US)

(73) Assignee: Brigham Young University, Provo, UT (US)

( * ) Notice: Subject to any disclaimer, the term of this patent is extended or adjusted under 35 U.S.C. 154(b) by 274 days.

(21) Appl. No.: 12/870,449

(22) Filed: Aug. 27, 2010

(65) Prior Publication Data

US 2011/0054573 A1 Mar. 3, 2011

Related U.S. Application Data

(60) Provisional application No. 61/275,639, filed on Aug. 31, 2009.

(51) Int. Cl.
*A61N 5/06* (2006.01)
*A61B 19/00* (2006.01)
*A61B 18/18* (2006.01)

(52) U.S. Cl.
USPC .................. 607/90; 607/88; 128/898; 606/3; 606/13

(58) Field of Classification Search
USPC ....................... 607/88–93; 128/898; 606/2–52
See application file for complete search history.

(56) References Cited

U.S. PATENT DOCUMENTS

| | | | |
|---|---|---|---|
| 5,358,503 A | 10/1994 | Bertwell et al. | |
| 6,114,326 A | 9/2000 | Schueler | |
| 6,155,976 A | 12/2000 | Sackner et al. | |
| 6,194,445 B1 | 2/2001 | Oertel et al. | |
| 6,346,283 B1 | 2/2002 | Hoffman et al. | |
| 6,586,478 B2 | 7/2003 | Ackman et al. | |
| 6,602,868 B2 | 8/2003 | McBrinn et al. | |
| 6,607,550 B1 | 8/2003 | Bertwell | |
| 6,855,735 B2 | 2/2005 | Friedman | |
| 2003/0092759 A1 | 5/2003 | Abuzzahab, Sr. | |
| 2004/0044384 A1 | 3/2004 | Leber et al. | |

(Continued)

FOREIGN PATENT DOCUMENTS

WO    WO 2008/148045    12/2008

OTHER PUBLICATIONS

Mitchell et al., "Comparison of two infrared devices in their effectiveness in reducing symptoms associated with RLS", Informa Healthcare; Physiotherapy Theory and Practice, Early Online, pp. 1-8, 2010.

(Continued)

*Primary Examiner* — Dawayne A Pinkney

(57) ABSTRACT

Disclosed herein are systems and methods for reducing effects of restless legs syndrome (RLS) in a subject. The method includes identifying, on the subject, a body region affected by RLS, placing an emitter unit in direct contact with skin of the body region, wherein the emitter unit includes at least one emitter that emits near-infrared light, and activating the emitter to emit an effective amount of near-infrared light for inducing release of nitric oxide from hemoglobin or generation in the endothelium. Also disclosed is an emitter unit that is placed in direct contact with a subject's skin associated with RLS to reduce the effects of RLS. The emitter unit emits an effective amount of near-infrared light directed to the subject's skin to induce release of nitric oxide from hemoglobin or generation in the endothelium, and a module configured to toggle the emitter unit between a transmitting and a nontransmitting mode.

16 Claims, 6 Drawing Sheets

(56) References Cited

U.S. PATENT DOCUMENTS

| | | | |
|---|---|---|---|
| 2004/0122492 A1* | 6/2004 | Harth et al. | 607/88 |
| 2005/0197682 A1 | 9/2005 | Fox et al. | |
| 2006/0206174 A1 | 9/2006 | Honeycutt et al. | |
| 2006/0265029 A1 | 11/2006 | Huang et al. | |
| 2006/0287696 A1* | 12/2006 | Wright et al. | 607/88 |
| 2007/0055327 A1 | 3/2007 | Esch et al. | |
| 2007/0162093 A1* | 7/2007 | Porter et al. | 607/89 |
| 2009/0110933 A1 | 4/2009 | Hyde et al. | |
| 2013/0019374 A1* | 1/2013 | Schwartz | 2/69 |

OTHER PUBLICATIONS

Mitchell et al., "Restless legs syndrome and near-infrared light: An alternative treatment option", Informa Healthcare; Physiotherapy Theory and Practice, Early Online, pp. 1-7, 2010.

* cited by examiner

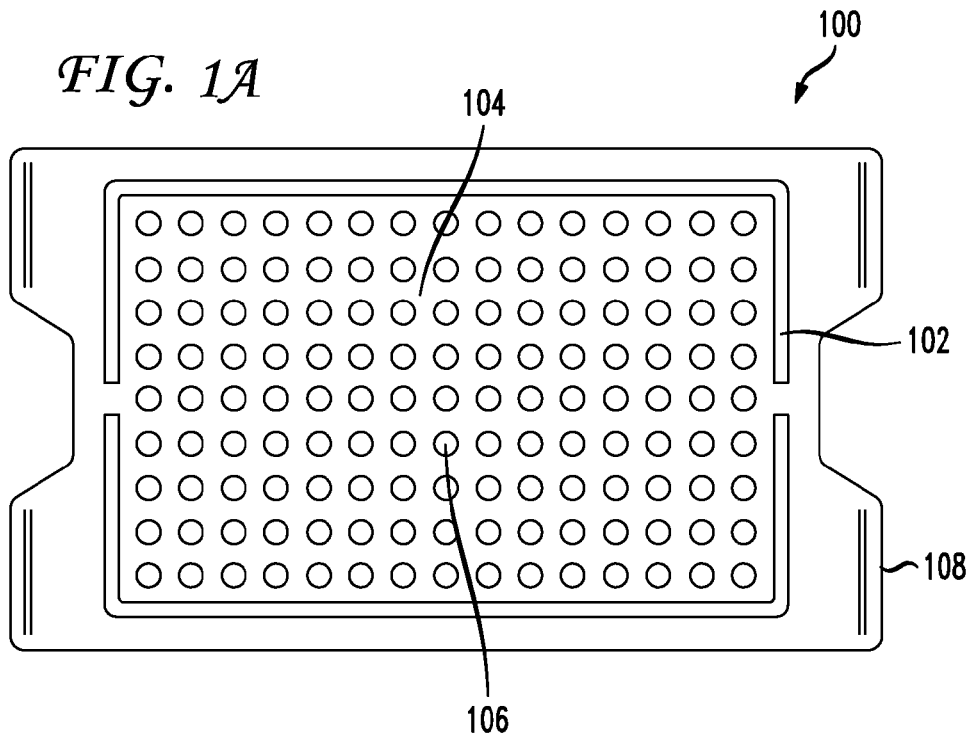
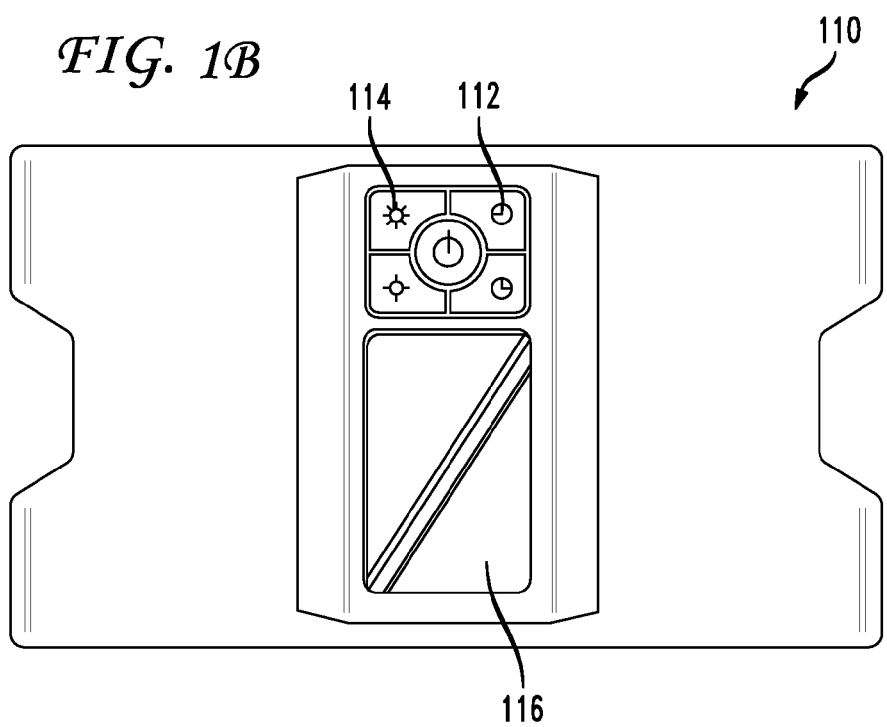

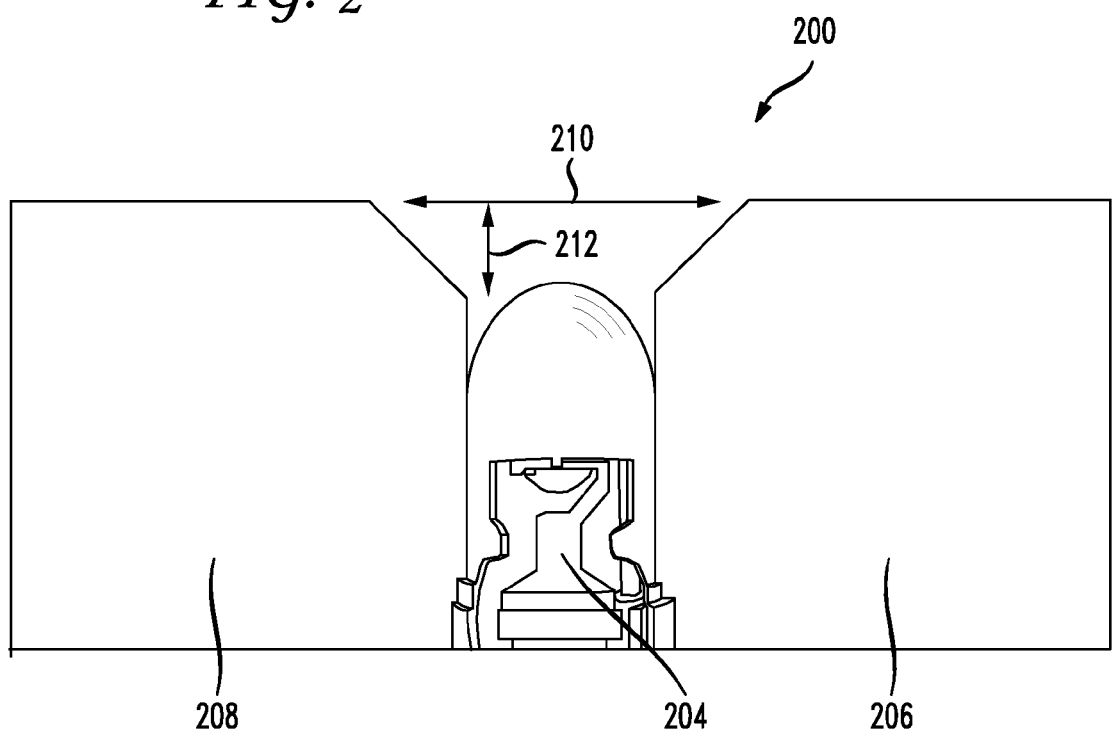

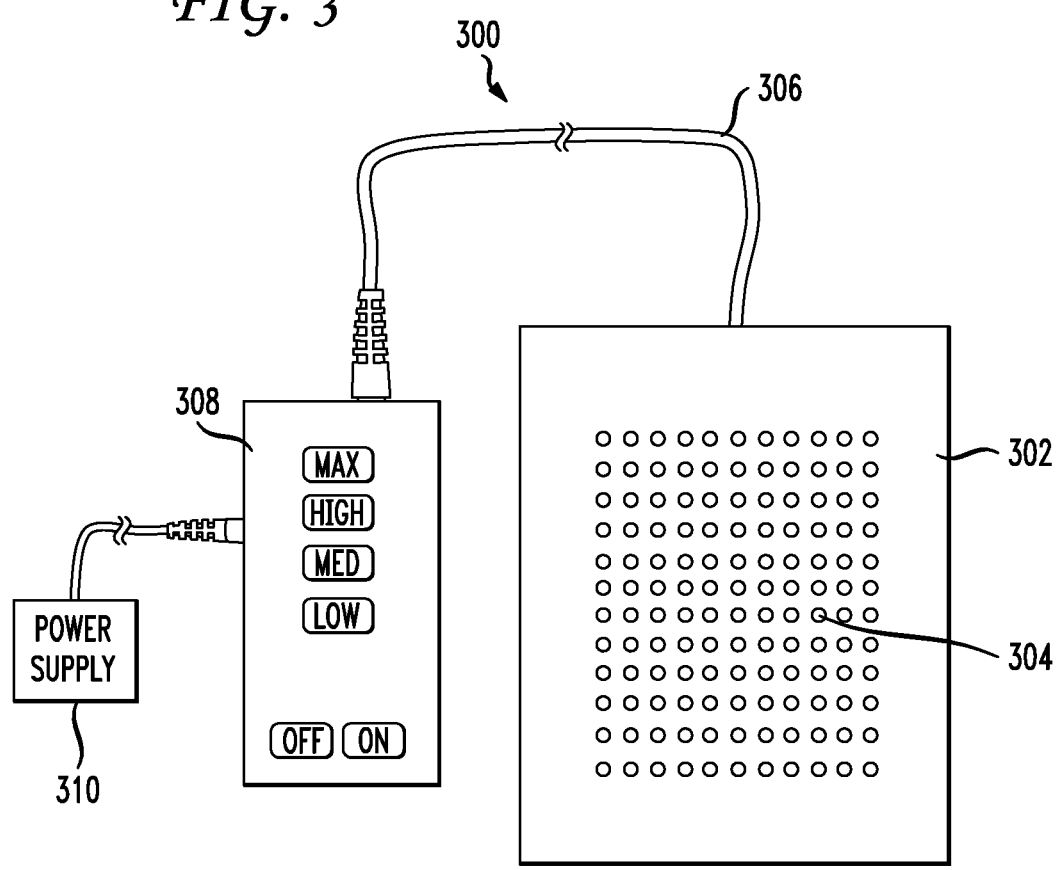

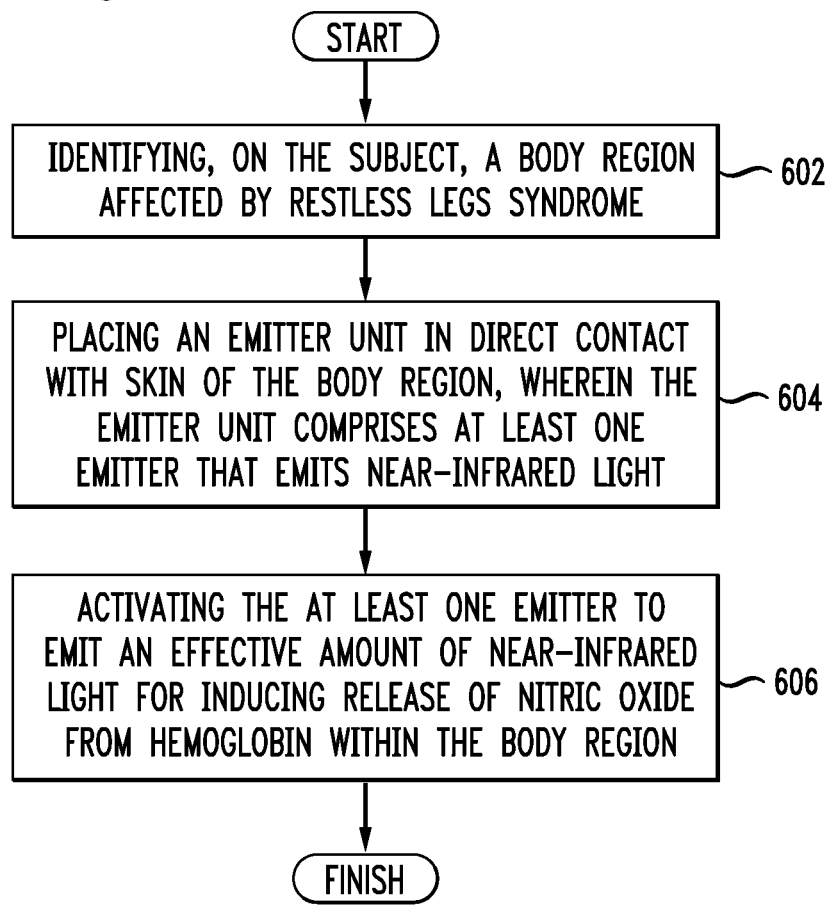

SYSTEM AND METHOD FOR TREATING SYMPTOMS OF RESTLESS LEGS SYNDROME

RELATED APPLICATIONS

This application claims priority to U.S. Provisional Application No. 61/275,639, filed 31 Aug. 2009, the entire contents of which are incorporated herein by reference.

BACKGROUND

1. Technical Field

The present disclosure relates to restless legs syndrome (RLS) and more specifically to treating RLS with near-infrared light.

2. Introduction

Restless Legs Syndrome (RLS), also known as Wittmaack-Ekbom's syndrome, is characterized by unpleasant sensations in the legs, limbs, or other parts of the body that typically occur at rest or before sleep and which may be relieved by activity such as walking. RLS has tormented people for centuries. RLS sufferers feel these creeping, crawling, aching, tugging, pulling, fidgety sensations deep within the legs, a strong urge to move accompanied or caused by uncomfortable or even distressing paresthesia of the legs or other body parts. The symptoms often become worse as the day progresses, leading to sleep disturbances or sleep deprivation and hence to strong fatigue, tiredness and low energy during the daytime. Movement usually lessens the symptoms. Exercise or movement are therefore potent management alternatives, but are unattractive when the patient wants to sleep.

One current RLS treatment option is medication, such as Requip® (ropinirole hydrochloride) and Mirapex® (pramipexole), both dopamine agonists. Unfortunately, these drugs can cause nausea and dizziness. Thus, many patients consider them to be a last resort. Other non-pharmacological treatment options include improving sleep quality by controlling sleep times, reducing caffeine and alcohol consumption, as well as maintaining a daily moderate exercise program. These treatment options are not entirely effective. Thus, what is needed in the art is an alternative or supplemental approach for treating RLS.

SUMMARY

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

Due to RLS's common manifestation in legs, the specification discusses RLS in terms of legs, but the principles disclosed herein are applicable to RLS occurring in any location of the body.

Disclosed are systems, methods, and non-transitory computer-readable storage media for reducing effects of restless legs syndrome in a subject. The method includes identifying, on the subject, a body region affected by restless legs syndrome. The method then includes placing an emitter unit in direct contact with skin of the body region, wherein the emitter unit includes at least one emitter that emits near-infrared light, and activating the at least one emitter to emit an effective amount of near-infrared light for inducing release of nitric oxide from hemoglobin within the body region and/or generation in the endothelium. The system can be an emitter unit for reducing the effects of restless legs syndrome in a subject by placing the emitter unit in direct contact with a portion of the subject's skin associated with a body region affected by restless legs syndrome. The emitter unit can include at least one emitter that emits an effective amount of near-infrared light directed to the subject's skin for inducing release of nitric oxide from hemoglobin within a body region. The emitter unit can be at least partially adjustable to contours of the subject's skin. The near-infrared light can be of a wavelength between approximately 700 nanometers and 1000 nanometers. The system can further include a module configured to toggle the at least one emitter between a transmitting mode and a nontransmitting mode.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which:

FIG. 1A illustrates a front view of an example emitter unit;
FIG. 1B illustrates a back view of the example emitter unit;
FIG. 2 illustrates a close-up view of an individual emitter in the example emitter unit;
FIG. 3 illustrates a single pad emitter configuration;
FIG. 6 illustrates an example method embodiment.

DETAILED DESCRIPTION

Figure 4:
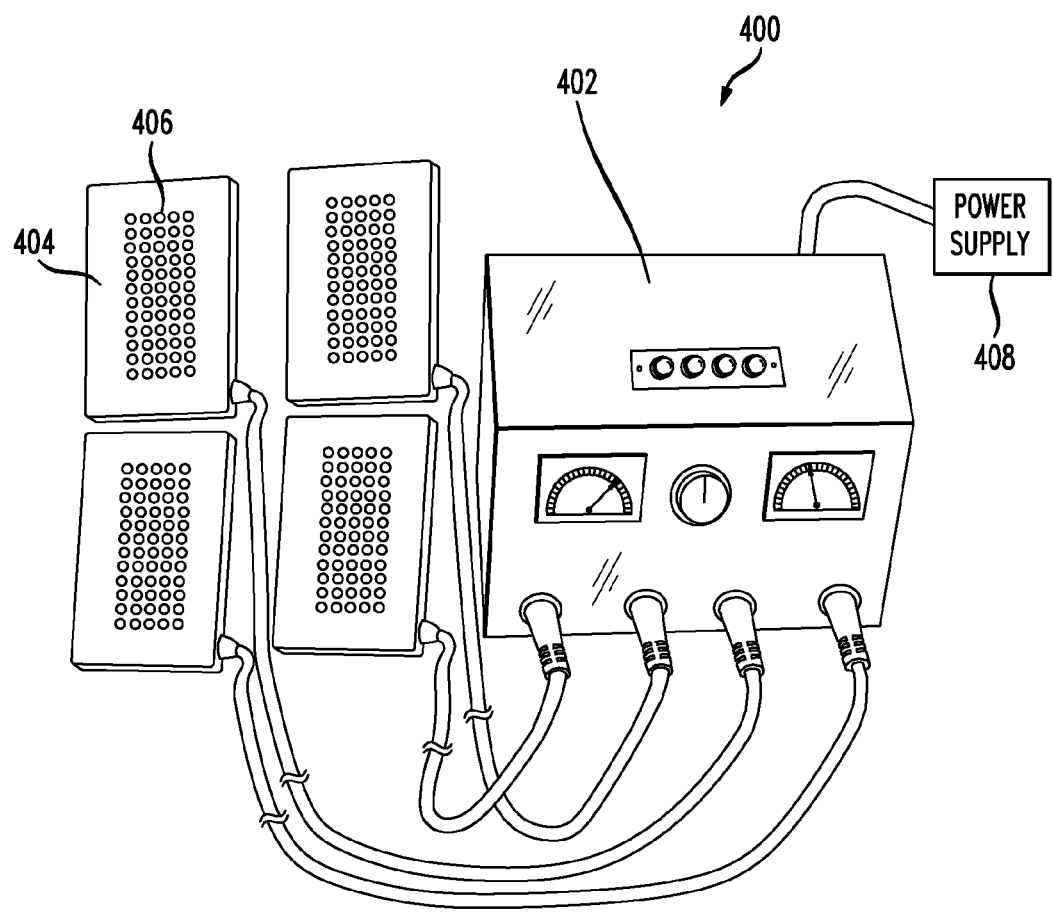
FIG. 4 illustrates a multiple pad emitter configuration.

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure.

The present disclosure addresses the need in the art for treating the symptoms of restless legs syndrome (RLS). The approaches set forth herein apply infrared and/or near-infrared light treatment to reduce the symptoms of RLS. An array of light emitting diodes (LEDs) can emit near-infrared light that penetrates the skin through an "optical window", which allows light at a particular wavelength to penetrate deeper into the tissue than visible light. Near-infrared light induces the release of Nitric Oxide (NO) which causes vasodilation of the blood vessels. The dilated blood vessels increase blood circulation, thereby satisfying the urge to move and reducing and/or eliminating the effects of RLS.

Nitric oxide (NO) is one factor responsible for vasodilation and consequent increased local blood flow. The enzyme nitric oxide synthase (NOS-3) produces NO, and is activated, among other factors, by shearing forces acting on the vascular endothelium generated by blood flow. The RLS-related urge to move may be a subconsciously driven mechanism to augment blood flow and tissue perfusion. The discomfort that accompanies the urge to move could be caused by the relative lack of oxygen to the superficial or deeper tissue, which would be offset by the increased blood flow. Near-infrared light increases blood flow by increasing bioactive NO in the blood, leading to vasodilation. Near-infrared light either activates NOS-3 in the endothelium or releases free NO from hemoglobin by intensive illumination. Therefore, the NO released as a result of near-infrared light treatment can, at least temporarily, decrease symptoms associated with RLS. Further, near-infrared light treatment can provide a systemic effect and secondary anabolic effects in addition to the primary effects of direct absorption of photons in the tissue. This systemic effect can lead to continued NO production or other changes in the tissue, leading to decreased RLS symptoms. NO can also influence nerve impulse transfer, by helping neuronal signal transduction, and assisting in converting nerve signals as they cross synapses. This quality of NO can further reduce symptoms associated with RLS.

A description of an example near-infrared light emitter unit for use in treatment of RLS is provided. Next, the disclosure discusses a close-up view of an individual emitter, followed by a discussion of two additional exemplary emitters. Also disclosed herein is a basic general purpose system or computing device in FIG. 5 which can be employed to practice all or part of the concepts and functionality disclosed herein. A more detailed description of the exemplary method will then follow. Variations shall be discussed herein as the various embodiments are set forth. The disclosure now turns to the example emitter unit shown in FIGS. 1A and 1B.

FIG. 1A shows the front 100 of the example emitter unit and FIG. 1B shows the back 110 of the example emitter unit. The emitter unit can be a home-based near-infrared light device for treatment of RLS. The emitter unit can include an array of LEDs 106 or other emitters that emit infrared and/or near-infrared light at a wavelength specific to the optic window of human tissue. The array of LEDs can be connected to a doubly flexible circuit board 104 attached to an insulating foam cover 108 to prevent thermal burns. The circuit board 104 can be flexible in the X and Y directions to allow full contouring to treatment area. The emitter unit can include portions of extra grip rubber 102 or other suitable regions of non-slip material such that the emitter unit stays in position on skin. In one implementation, the LEDs are mounted such that the emitter unit can be comfortably wrapped around the lower and/or upper leg of an RLS sufferer.

The back 110 of the example emitter unit in FIG. 1B shows a control module 116 for the example emitter unit. The control module 116 can include a power source, such as a custom lithium-ion battery pack (which may be user-removable or non-user-removable), standard removable batteries (such as AA, AAA, 9V, C, D, CR2025, CR2032, and so forth), an adapter to convert electricity from an external AC power source, and/or other power sources. A lithium-ion battery pack or other portable electricity generation or storage device can allow for user mobility during treatment. The control module 116 can also include adjustable treatment time controls 112 and adjustable treatment intensity controls 114. These controls can have a manual aspect and/or an automatic aspect. For example, the treatment time controls 112 and/or the treatment intensity controls 114 can include manual settings as well as automatic or selectable safety features such as adjustable treatment time shutoff to prevent thermal burns from overuse, a delayed start timer, automatic overheating temperature shutoff, adjustable treatment intensities, and other settings for intensity, pulsing, frequency, duration, and so on. These features allow safe, affordable, home-based treatments for RLS sufferers. Adjustable treatment intensity allows use with various levels of skin sensitivity.

In one embodiment, the control module 116 can provide for a combination of emitted light frequencies ranging, for example, from 50 Hz to 5000 Hz. The control module 116 can provide for different intensity levels on a per-region or per-emitter basis. Intensity can be measured as energy delivered in milliwatts (mW) per emitter or per region. A user suffering from RLS can apply near-infrared light on a regular schedule, such as thirty minute sessions three times per week for four weeks, for example. Near-infrared light treatments can be a maintenance measure to keep RLS symptoms from recurring and/or can be used on an as-needed basis when RLS symptoms strike.

FIG. 2 shows a close-up side view of one configuration 200 of an individual LED emitter 204 in the LED array 106 such that the LEDs do not directly contact the skin. The LED 204 is between two sides 206, 208 of foam padding or some other material. In one aspect, the material is a thick vinyl outer layer enclosing gel, beads, or some other similar filler. In one aspect, the padding is provided only for comfort of the user, and in other aspects, the padding provides some supplemental or secondary effect, such as delivering epicutaneous drugs. The padding can be removable and replaceable. For example, a user can remove a hard, relatively inflexible padding element and replace it with a softer, flexible padding element. Different padding elements can be made of different materials, have different thicknesses, different levels of flexibility. For example, one padding element can be designed for calves or feet while another padding element can be designed for thighs. One padding material may be advantageous for sensitive skin, as another example. The different shapes and sizes of the intended body part can influence the attributes of a padding element intended for use with that body part. As stated above, the foam padding can serve as thermal insulation to prevent the leg from heating up due to the electronic components.

The LED 204 is recessed a distance 212 from the top of the two sides 206, 208 such that if the top is touching skin the LED 204 remains the distance 212 from the skin and does not contact the skin. Further, the opening at the top of the padding can be a wider distance 210 than the width of the LED 204. In other variations, the opening can be the same width as the LED 204 or a smaller width than the LED 204. The LED array can include LEDs that are uniformly recessed and with uniform opening widths or the LED array can include different recess and/or opening distances. In one variation, the emitter unit can include a mechanism to vary these distances dynamically. For example, a motor or other mechanism can adjust position of the LEDs to increase or decrease the distance 212 from the top. In one aspect, in order to prevent direct skin contact with the LED, a near-infrared light transmissible layer, such as glass or plastic, covers all or part of the opening width 210. In another aspect, a mechanical, electrical, or other mechanism can increase or decrease the width 210 of the opening.

The shape and size of the recessed area can be different from the angled shape shown in FIG. 2. For example, the recessed area can be larger or smaller. Each recessed area can include multiple sub-angles. Further, the shape of the recessed area can include curves, soft corners, and/or other shapes. In one aspect, the recessed area for each LED is slightly different based on an intended use. In another aspect, the recessed area for the LEDs is configured such that when the emitter unit is wrapped around a leg, the sides 206, 208 of the recessed area compress to form a desired shape and size. The sides 206, 208 can be part of a user-removable pad so that the user can replace the pad with another pad having a different configuration for the recessed areas.

FIG. 3 illustrates a single pad emitter configuration 300. In this configuration 300, a single emitter pad 302 having an array of individual emitters 304 is connected via a power cable 306 to a control module 308. Alternately, the emitter pad 302 includes its own power supply and receives instructions from the control module 308 wirelessly. The control module 308 is connected to a power supply 310 for powering and/or communicating with the individual emitters 304 or sensors embedded in the emitter pad 302. While FIG. 3 depicts cables 306, any of the elements shown can be integrated into a single unit without external cables or the elements can communicate wirelessly. The control module 308 can accept inputs from multiple types of power supplies 310. For example, the control module 308 can include a battery pack as well as an AC power input receptacle. The emitter pad 302 can include an adjustable strap to attach the pad to a user's body. Some examples of adjustable strap include a buckle, Velcro, buttons, elastic, and so forth. The emitter pad 302 can be integrated as part of an article of clothing, such as a jacket, pants, shoes, or socks. The control module 308 allows the user to directly or indirectly control the individual emitters 304 as a group, as regions, or individually. Further, a user-operated remote control module (not shown) can interact wirelessly with the control module 308. A user experiencing RLS symptoms in her leg can strap the emitter pad 302 on the affected area and turn on one or more or all of the individual emitters via the control module 308.

In one aspect, the user stores different profiles in the control module 308 for different needs. For example, if a particular configuration is particularly effective for night time RLS symptoms in the lower leg, the user can save that configuration in a profile and easily retrieve those settings for later reuse. A profile can include a single setting or a series of settings in a particular order for a particular therapeutic goal. For example, one profile can specify a particular frequency and intensity for a particular duration, where another profile has a series of different settings, such as a first time period alternating between low and high intensity, a second time period at high intensity, followed by a third time period that slowly decreases from high intensity to low intensity. A user can name specific profiles. In addition to a name, the system can tag a profile with metadata such as which user created the profile, when it was created, where it was created, and other available information. Profiles can be tied to a specific user and can require a password or passphrase to activate. In one aspect, the system suggests a profile based on a particular user, a particular time of day, and/or other information available to the system. In addition to user-created or modified profiles, the control module 308 can include predefined settings, such as moderate RLS, severe RLS, upper leg, lower leg, preventative treatment, and so forth.

FIG. 4 illustrates a multiple pad emitter configuration 400. In this configuration 400, a group of emitter pads 404, each having a respective array of individual emitters 406 are connected, such as via a wired or a wireless link, to a control unit 402 which instructs the emitter pads 404 how and when to emit near-infrared light based on input from a human user. The control unit 402 can receive electrical power from a power supply 408 such as a battery, AC adapter, or other source. A user can strap or otherwise attach the emitter pads 404 to body regions affected by RLS for treatment with the near-infrared light emitted from the emitter pads 404. The near-infrared light is directed to the subject's skin in order to induce the release of nitric oxide from hemoglobin within or circulating through the body region. The control unit 402 can toggle one or more emitter, pad, pad region, and/or multiple pads between a transmitting mode and a non-transmitting mode. In one embodiment, the control unit 402 instructs one emitter pad to emit near-infrared light at a first frequency and/or intensity, instructs another emitter pad to emit near-infrared light at a second frequency and/or intensity, and so on. One example scenario where this approach can be used is when one body region responds better to near-infrared light at 900 nanometers, and another body region responds better to near-infrared light at 1000 nanometers. A first emitter pad can be configured to transmit at 900 nanometers independently of a second emitter pad transmitting at 1000 nanometers.

Figure 5:
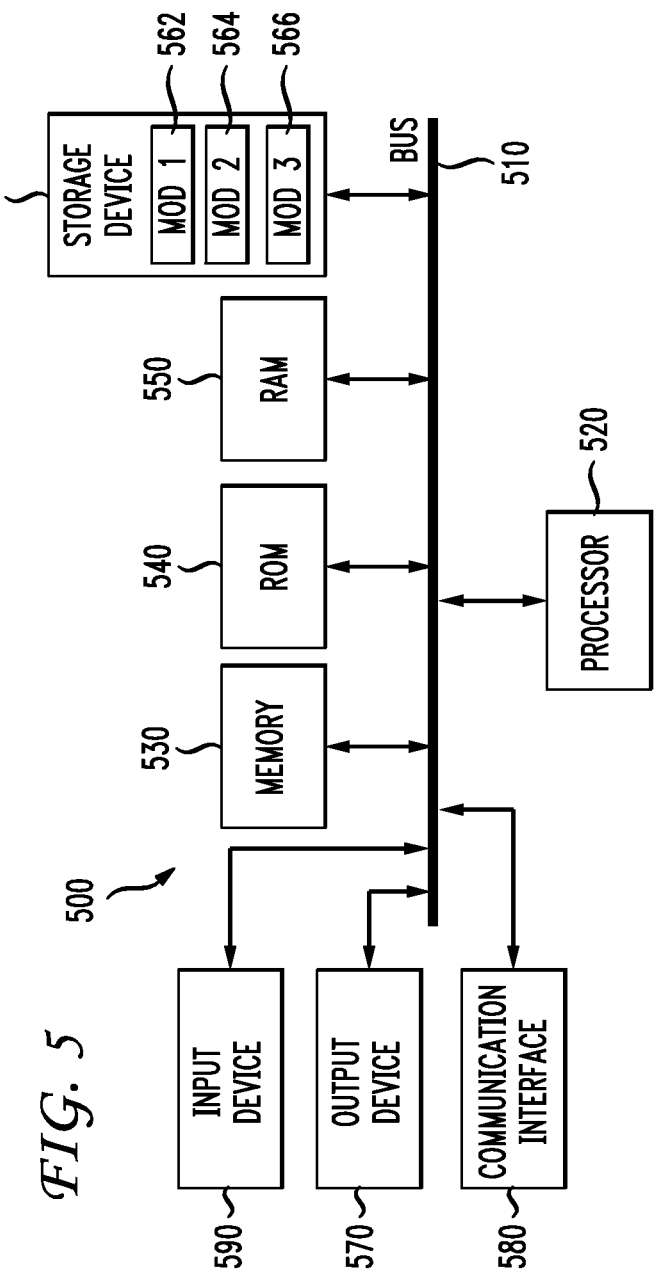
FIG. 5 illustrates an example computing system embodiment.

The disclosure now turns to a discussion of an exemplary computing, all or part of which can control the components and/or provide functionality described herein. With reference to FIG. 5, an exemplary system 500 includes a general-purpose computing device 500, including a processing unit (CPU or processor) 520 and a system bus 510 that couples various system components including the system memory 530 such as read only memory (ROM) 540 and random access memory (RAM) 550 to the processor 520. The system 500 can include a cache of high speed memory connected directly with, in close proximity to, or integrated as part of the processor 520. The system 500 copies data from the memory 530 and/or the storage device 560 to the cache for quick access by the processor 520. In this way, the cache provides a performance boost that avoids processor 520 delays while waiting for data. These and other modules can control or be configured to control the processor 520 to perform various actions. Other system memory 530 may be available for use as well. The memory 530 can include multiple different types of memory with different performance characteristics. It can be appreciated that the disclosure may operate on a computing device 500 with more than one processor 520 or on a group or cluster of computing devices networked together to provide greater processing capability. The processor 520 can include any general purpose processor and a hardware module or software module, such as module 1 562, module 2 564, and module 3 566 stored in storage device 560, configured to control the processor 520 as well as a special-purpose processor where software instructions are incorporated into the actual processor design. The processor 520 may essentially be a completely self-contained computing system, containing multiple cores or processors, a bus, memory controller, cache, etc. A multi-core processor may be symmetric or asymmetric.

The system bus 510 may be any of several types of bus structures including a memory bus or memory controller, a peripheral bus, and a local bus using any of a variety of bus architectures. A basic input/output (BIOS) stored in ROM 540 or the like, may provide the basic routine that helps to transfer information between elements within the computing device 500, such as during start-up. The computing device 500 further includes storage devices 560 such as a hard disk drive, a magnetic disk drive, an optical disk drive, tape drive or the like. The storage device 560 can include software modules 562, 564, 566 for controlling the processor 520. Other hardware or software modules are contemplated. The storage device 560 is connected to the system bus 510 by a drive interface. The drives and the associated computer readable storage media provide nonvolatile storage of computer readable instructions, data structures, program modules and other data for the computing device 500. In one aspect, a hardware module that performs a particular function includes the software component stored in a non-transitory computer-readable medium in connection with the necessary hardware components, such as the processor 520, bus 510, display 570, and so forth, to carry out the function. The basic components are known to those of skill in the art and appropriate variations are contemplated depending on the type of device, such as whether the device 500 is a small, handheld computing device, a desktop computer, or a computer server.

Although the exemplary embodiment described herein employs the hard disk 560, it should be appreciated by those skilled in the art that other types of computer readable media which can store data that are accessible by a computer, such as magnetic cassettes, flash memory cards, digital versatile disks, cartridges, random access memories (RAMs) 550, read only memory (ROM) 540, a cable or wireless signal containing a bit stream and the like, may also be used in the exemplary operating environment. Non-transitory computer-readable storage media expressly exclude media such as energy, carrier signals, electromagnetic waves, and signals per se.

To enable user interaction with the computing device 500, an input device 590 represents any number of input mechanisms, such as a microphone for speech, a touch-sensitive screen for gesture or graphical input, keyboard, mouse, motion input, speech and so forth. An output device 570 can also be one or more of a number of output mechanisms known to those of skill in the art. In some instances, multimodal systems enable a user to provide multiple types of input to communicate with the computing device 500. The communications interface 580 generally governs and manages the user input and system output. There is no restriction on operating on any particular hardware arrangement and therefore the basic features here may easily be substituted for improved hardware or firmware arrangements as they are developed.

For clarity of explanation, the illustrative system embodiment is presented as including individual functional blocks including functional blocks labeled as a "processor" or processor 520. The functions these blocks represent may be provided through the use of either shared or dedicated hardware, including, but not limited to, hardware capable of executing software and hardware, such as a processor 520, that is purpose-built to operate as an equivalent to software executing on a general purpose processor. For example the functions of one or more processors presented in FIG. 5 may be provided by a single shared processor or multiple processors. (Use of the term "processor" should not be construed to refer exclusively to hardware capable of executing software.) Illustrative embodiments may include microprocessor and/or digital signal processor (DSP) hardware, read-only memory (ROM) 540 for storing software performing the operations discussed below, and random access memory (RAM) 550 for storing results. Very large scale integration (VLSI) hardware embodiments, as well as custom VLSI circuitry in combination with a general purpose DSP circuit, may also be provided.

The logical operations of the various embodiments are implemented as: (1) a sequence of computer-implemented steps, operations, or procedures running on a programmable circuit within a general use computer, (2) a sequence of computer-implemented steps, operations, or procedures running on a specific-use programmable circuit; and/or (3) interconnected machine modules or program engines within the programmable circuits. The system 500 shown in FIG. 5 can practice all or part of the recited methods, can be a part of the recited systems, and/or can operate according to instructions in the recited non-transitory computer-readable storage media. Such logical operations can be implemented as modules configured to control the processor 520 to perform particular functions according to the programming of the module. For example, FIG. 5 illustrates three modules Mod1 562, Mod2 564 and Mod3 566 which are modules configured to control the processor 520. These modules may be stored on the storage device 560 and loaded into RAM 550 or memory 530 at runtime or may be stored as would be known in the art in other computer-readable memory locations.

The disclosure now turns to the exemplary method embodiment shown in FIG. 6. For the sake of clarity, the method is discussed in terms of an exemplary system such as is shown in FIG. 5 configured to practice the method. FIG. 6 illustrates an example method embodiment for reducing effects of restless legs syndrome in a subject. For clarity, the method is discussed in terms of a system 500 configured to practice the method, although a system and/or a human user can practice one or more of the steps of the method. The system 500 first identifies, on the subject, a body region affected by restless legs syndrome (602). The body region can be a leg and/or another area of the subject's body.

The system 500 places an emitter unit in direct contact with skin of the body region, wherein the emitter unit includes at least one emitter that emits near-infrared light (604). One or more of the emitters can be aimed at the skin, but others can be aimed in a different direction and reflected at the skin, for example. The emitter unit can include an array of individual emitters, such as LEDs. Other suitable emitters can be used in addition to or in place of LEDs. The array of emitters can be doubly flexible along an x axis and a y axis. Further, the array of emitters can be adjustable to contours of the skin. The emitter unit can include a gripping area, such as a rubber region, that contacts the skin to hold the emitter unit in place or to prevent the emitter unit from slipping. Inasmuch as the emitter unit and/or the individual emitters may produce some heat, the emitter unit can include an insulating cover to prevent burns. The insulating cover can be foam, leather, fabric, and/or gel, as well as any other suitable material.

The system 500 activates the at least one emitter to emit an effective amount of near-infrared light for inducing release of nitric oxide from hemoglobin within the body region (606). The near-infrared light can have a wavelength between approximately 700 nanometers and 1000 nanometers. In one variation, the system 500 activates multiple emitters to emit different, adjustable frequencies, wavelengths, and/or intensities of near-infrared light simultaneously from different individual emitters. In another variation, the system 500 activates emitters to periodically pulse on and off at a fixed or adjustable duration instead of emitting steadily.

The emitter unit can further include an automatic shut-off timer to prevent overexposure to near-infrared light. A user can set a duration for the automatic shut-off timer, such as 30 or 60 minutes. The emitter unit can incorporate a temperature sensor and a module configured to turn off one or more emitter if the temperature sensor indicates an overheating condition. For example, the module can turn gradually turn off one or more emitter at a time until the temperature sensor indicates that the heat levels are acceptable. As another example, the module can turn off all the emitters if the temperature is above a certain threshold.

These approaches can reduce the many negative impacts of RLS, such as sleep loss or the inability to travel comfortably either by car or airplane. Near-infrared light treatment can be used in conjunction with other RLS treatments, such as iron supplements or medication such as dopaminergic agents, narcotics, benzodiazepines, or sedatives. Further, near-infrared light treatment does not induce any side effects. Current drug treatments for RLS have an annual prescription cost of about $1,000, but near-infrared treatment devices cost substantially less, representing a huge savings to insurance companies and RLS sufferers.

Embodiments within the scope of the present disclosure may also include tangible and/or non-transitory computer-readable storage media for carrying or having computer-executable instructions or data structures stored thereon. Such non-transitory computer-readable storage media can be any available media that can be accessed by a general purpose or special purpose computer, including the functional design of any special purpose processor as discussed above. By way of example, and not limitation, such non-transitory computer-readable media can include RAM, ROM, EEPROM, CD-ROM or other optical disk storage, magnetic disk storage or other magnetic storage devices, or any other medium which can be used to carry or store desired program code means in the form of computer-executable instructions, data structures, or processor chip design. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

Computer-executable instructions include, for example, instructions and data which cause a general purpose computer, special purpose computer, or special purpose processing device to perform a certain function or group of functions. Computer-executable instructions also include program modules that are executed by computers in stand-alone or network environments. Generally, program modules include routines, programs, components, data structures, objects, and the functions inherent in the design of special-purpose processors, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Those of skill in the art will appreciate that other embodiments of the disclosure may be practiced in network computing environments with many types of computer system configurations, including personal computers, hand-held devices, multi-processor systems, microprocessor-based or programmable consumer electronics, network PCs, mini-computers, mainframe computers, and the like. Embodiments may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

The various embodiments described above are provided by way of illustration only and should not be construed to limit the scope of the disclosure. For example, the principles herein can be adapted as near-infrared light medical equipment for use in a home, rehabilitation center, doctor's office, and so forth. Those skilled in the art will readily recognize various modifications and changes that may be made to the principles described herein without following the example embodiments and applications illustrated and described herein, and without departing from the spirit and scope of the disclosure.

I claim:

1. A method of reducing effects of restless legs syndrome in a subject, the method comprising:
    identifying, on the subject, a body region of the subject affected by restless legs syndrome;
    placing an emitter unit in direct contact with skin of the body region, wherein the emitter unit comprises at least one emitter that emits near-infrared light at a wavelength of 890 nanometers, and wherein the emitter unit comprises a pad to deliver, directly to the skin of the body region of the subject, an epicutaneous drug for treating restless legs syndrome; and
    activating the at least one emitter to emit an effective amount of near-infrared light for a treatment duration of at least thirty minutes to induce generation of nitric oxide from at least one of hemoglobin and the endothelium within the body region, wherein the near-infrared light penetrates into tissue of the body region deeper than visible light would penetrate.

2. The method of claim 1, wherein the emitter unit further comprises an array of emitters.

3. The method of claim 2, wherein the array of emitters is doubly flexible along an x axis and a y axis.

4. The method of claim 2, wherein the array of emitters is adjustable to contours of the skin.

5. The method of claim 1, wherein the emitter unit further comprises an automatic shut-off timer.

6. The method of claim 1, wherein the emitter unit further comprises a temperature sensor and a module configured to turn off the at least one emitter if the temperature sensor indicates an overheating condition.

7. The method of claim 1, wherein the at least one emitter transmits via at least one of adjustable intensity and adjustable frequency.

8. The method of claim 1, wherein the emitter unit further comprises a gripping area that contacts the skin.

9. The method of claim 1, wherein the emitter unit further comprises an insulating cover.

10. The method of claim 1, wherein the at least one emitter is at least one light emitting diode.

11. An emitter unit for reducing the effects of restless legs syndrome in a subject by placing the emitter unit in direct contact with a portion of the skin of the subject associated with a body region affected by restless legs syndrome, the system comprising:
    at least one emitter adjustable to contours of the skin of the subject that emits an effective amount of near-infrared light directed to the skin of the subject for a treatment duration of at least thirty minutes to induce generation of nitric oxide from at least one of hemoglobin and the endothelium within the body region, wherein the effective amount of near-infrared light has a wavelength of 890 nanometers, and wherein the near-infrared light penetrates into tissue of the body region deeper than visible light would penetrate;
    a pad which, when placed in contact with the skin of the subject, delivers, directly to the skin of the subject, an epicutaneous drug for treating restless legs syndrome; and
    a module configured to toggle the at least one emitter between a transmitting mode and a nontransmitting mode.

12. The emitter unit of claim 11, wherein the at least one emitter further comprises an array of emitters.

13. The emitter unit of claim 12, wherein the array of emitters is doubly flexible along an x axis and a y axis.

14. The emitter unit of claim 11, wherein the at least one emitter is at least one light emitting diode.

15. The emitter unit of claim 11, wherein the emitter unit further comprises an automatic shut-off timer.

16. The emitter unit of claim 11, wherein the emitter unit further comprises a temperature sensor and a shutoff module configured to turn off the at least one emitter if the temperature sensor indicates an overheating condition.

* * * * *